United States Patent [19]  
Poolman et al.

[11] 3,974,054  
[45] Aug. 10, 1976

[54] MEASURING CELL FOR DETERMINING OXYGEN CONCENTRATIONS IN A GAS MIXTURE

[75] Inventors: Petrus Jacobus Poolman; Nabil Ahmed Abdalla; Arend Harrewijne, all of Eindhoven, Netherlands

[73] Assignee: U.S. Philips Corporation, New York, N.Y.

[22] Filed: Dec. 12, 1974

[21] Appl. No.: 531,821

[30] Foreign Application Priority Data  
Jan. 7, 1974  Netherlands....................... 7400147

[52] U.S. Cl. ........................................... 204/195 S  
[51] Int. Cl.² ........................................ G01N 27/46  
[58] Field of Search ......... 136/86 F; 204/1 T, 195 S

[56] References Cited  
UNITED STATES PATENTS  
3,558,280  1/1971  Panson et al. .................. 204/195 S  
3,691,023  9/1972  Ruka et al. ...................... 204/195 S  
3,719,564  3/1973  Lilly et al. ............................ 204/1 T  
3,738,341  6/1973  Loos ................................. 204/195 S  
3,791,953  2/1974  Minushkin et al. .............. 204/195 S FOREIGN PATENTS OR APPLICATIONS  
2,173,564  10/1973  France............................. 204/195 S Primary Examiner—T. Tung  
Attorney, Agent, or Firm—Frank R. Trifari; Ronald L. Drumheller

[57] ABSTRACT

Measuring cell for determining oxygen concentrations in a gas mixture having a partition consisting of an electrolyte material such as $ZrO_2$, which reversibly reacts with oxygen and is ion conductive. The measuring cell is characterized in that the partition closes a hollow body and projects therefrom so that the electrodes may be provided on the same side to reduce disturbing influences on the measurement.

8 Claims, 1 Drawing Figure

U.S. Patent  Aug. 10, 1976  3,974,054
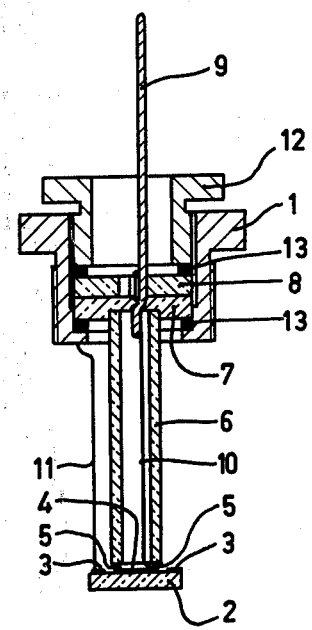

MEASURING CELL FOR DETERMINING OXYGEN CONCENTRATIONS IN A GAS MIXTURE

The invention relates to a measuring cell for determining oxygen concentrations in a gas mixture.

Such a cell is known, for example, from an article in the Journal of the Electrochem. Soc. 109, 723–726 (1962). It has a partition consisting of a solid material undergoing a reversible reaction with oxygen and exhibiting ion conductivity, which partition is provided on both sides with a thin gas-permeable metallic and/or semiconducting electrode coating. According to one embodiment such a solid material is stabilized zirconium oxide exhibiting conductivity by means of oxygen ions while the electrodes consist of noble metal such as porous platinum. The gas mixture whose partial or absolute oxygen pressure must be measured is present on one side of the partition. A reference gas having a known partial oxygen pressure is present on the other side. Air is preferably chosen for this purpose. At a sufficiently high temperature, i.e. 450° and 850°C for the embodiment with stabilized zirconium oxide, a voltage difference E is produced due to movement of the ions between the two electrodes, which difference in accordance with the Nernst equation $$E = \frac{RT}{2zF} \ln \frac{p_1}{p_2}$$

is dependent on the ratio of the partial pressures $p_1$ and $p_2$.

In this equation R is the gas constant in J mol$^{-1}$ K$^{-1}$, T is the absolute temperature, z is the valence of the oxygen ion and F is the Faraday constant in coulombs.

The cell may alternatively be used for measuring the concentration of carbon monoxide in a gas mixture because this carbon monoxide at low concentrations is in balance with oxygen according to the equation:

$$CO + \tfrac{1}{2}O_2 \rightarrow CO_2$$

An important use of the measuring cell according to the invention is a device in which the cell is placed in an exhaust gas pipe of an internal combustion engine so that a voltage dependent on the CO content is generated. This device which is extensively described in U.S. Pat. No. 3,738,341 has a member for controlling the air-fuel ratio and a feedback acting on this member so that the ratio is increased when the voltage generated by the cell increases.

U.S. Patent No. 3,819,500 describes an embodiment of such a measuring cell in which the partition consists of a flat sheet of ion-conducting material which is provided between two metal rings as a closure on one side of an open-ended metal bush, the outer metal ring making electrical contact with the bush and the inner metal ring being insulated relative to the bush, but being connected electrically to a conductor that leads through a sheet of insulating material having at least one gas-stream aperture and in which the metal rings, the sheet of ion-conducting material and the sheet provided with the lead-through conductor are optionally jointly clamped in the bush in a detachable manner with the aid of one or more spacers.

This embodiment, though very attractive, was found to have some drawbacks in practice. Since electrode material in the form of finely divided platinum is used, the gas-tightness of this construction is compromised. There is a great risk that leakage from the measuring side to the reference side of the ion-conducting sheet produces incorrect readings.

In this embodiment a temperature gradient is present across the ion-conducting sheet, which gradient causes a thermoelectrical voltage likewise giving rise to inaccuracies.

These drawbacks are eliminated in the embodiment according to the invention in which the partition between the measuring and reference gas atmospheres consists of a flat sheet of electrolyte material, which closes an opening in a body that is in communication with one of the two gas atmospheres. The sheet is, however, larger than the surface of the opening while the part projecting from the opening is in communication with the other of the two gas atmospheres.

The invention is characterized in that the measuring electrode and the reference electrode are both on the same side of the flat sheet.

The electrode surfaces consist of, for example, two concentrical cathodically sputtered platinum surfaces.

The invention will be further described with reference to a drawing.

In the FIGURE the reference numeral 1 denotes a metal bush, 2 is a sheet of stabilized ZrO$_2$, for example, ZrO$_2$ with 7.5% by weight of CaO, 3 and 4 are platinum coatings provided by cathodic sputtering on the zirconium oxide sheet, 5 is a platinum ring between the zirconium oxide sheet and an aluminum oxide pipe 6 having a flange 7 of aluminium cemented to 6. Sheet 2 and pipe 6 are connected together by means of thermal compression through the platinum ring 5.

According to a modification the sheet 2 and the pipe 6 are connected together by means of a glass ceramic material obtained from glass powder having the composition in % by weight:

| BaO | 59.0 | SiO$_2$ | 14.3 |
| B$_2$O$_3$ | 21.9 | ZnO | 4.8 |

To which 5% by weight of ZrO$_2$ powder has been added which is provided between the two parts whereafter the assembly is heated to the melting point of the mixture and is subsequently slowly cooled.

An insulating aluminum oxide sheet provided with gas-stream apertures is denoted by 8; 9 is a rigid conductor which is connected to electrode coating 4 by means of the flexible conductor 10. Another flexible conductor 11 connects the electrode coating 3 to the housing 1 connected to the ground. The voltage is measured between the electrode coatings 3 and 4. 12 is a nut and 13 are seals.

What is claimed is:

1. A cell for measuring the ratio between oxygen concentrations of two gas mixtures, comprising:
   a hollow body for communicating one of the gas mixtures to an opening therein;
   a flat partition sheet closing said opening and projecting therebeyond so that a first area of one side of said sheet is exposed to the gas mixture inside said hollow body while outside of said hollow body a second area of said one side may be simultaneously exposed to another gas mixture, said flat sheet being electrolyte material which reversibly reacts with oxygen and is ion conductive;

electrically separate gas permeable electrodes on said first and second areas respectively; and means for electrically contacting said electrodes to measure the voltage therebetween as a measure of the ratio between the oxygen concentrations to which said electrodes are exposed.

2. A cell as defined in claim 1 wherein said hollow body is electrically insulative.

3. A cell as defined in claim 1 wherein said sheet consists essentially of stabilized zirconium oxide.

4. A cell as defined in claim 3 wherein said electrodes consist essentially of porous platinum.

5. A cell as defined in claim 3 wherein said hollow body consists essentially of aluminum oxide.

6. A cell as defined in claim 5 and further characterized by said hollow body and said sheet being bonded to each other around said opening via a glass ceramic material.

7. A cell as defined in claim 5 and further characterized by said hollow body and said sheet being thermocompression bonded to each other around said opening via a platinum ring.

8. A cell as defined in claim 1 wherein said electrodes are concentric.

* * * * *